United States Patent
Oster et al.

(10) Patent No.: US 9,833,636 B2
(45) Date of Patent: Dec. 5, 2017

(54) MULTI-AXIS DYNAMIC TRACKING FOR RADIATION THERAPY

(75) Inventors: Matthias Oster, Palo Alto, CA (US); Herbert Cattell, Mountain View, CA (US); Qingxiang Ke, San Jose, CA (US); Stefan Jochem Thieme-Marti, Windisch (CH); Michelle Marie Svatos, Oakland, CA (US); Andres Graf, Oberwil (CH)

(73) Assignees: Varian Medical Systems, Inc., Palo Alto, CA (US); Varian Medical Systems International AG, Cham (CH)

( * ) Notice: Subject to any disclaimer, the term of this patent is extended or adjusted under 35 U.S.C. 154(b) by 296 days.

(21) Appl. No.: 13/614,773

(22) Filed: Sep. 13, 2012

(65) Prior Publication Data

US 2014/0070115 A1    Mar. 13, 2014

(51) Int. Cl.
  *A61N 5/00* (2006.01)
  *A61N 5/10* (2006.01)
  *A61B 6/00* (2006.01)

(52) U.S. Cl.
  CPC .......... *A61N 5/1045* (2013.01); *A61B 6/4452* (2013.01); *A61B 6/4458* (2013.01); *A61N 5/107* (2013.01); *A61N 5/1067* (2013.01)

(58) Field of Classification Search
  CPC .................................. G21K 1/00; A61N 5/10
  USPC ...................................................... 250/492.1
  See application file for complete search history.

(56) References Cited

U.S. PATENT DOCUMENTS

| | | | | |
|---|---|---|---|---|
| 8,331,532 B2* | 12/2012 | Nord | ............... | A61N 5/1037 378/65 |
| 8,789,223 B2* | 7/2014 | Erbel | ............... | A61B 6/0421 378/20 |
| 2007/0041500 A1* | 2/2007 | Olivera | ............... | A61N 5/1042 378/65 |
| 2009/0067577 A1 | 3/2009 | Rigney et al. | | |
| 2010/0176309 A1 | 7/2010 | Mackie et al. | | |
| 2011/0015521 A1* | 1/2011 | Faul | ............... | A61B 34/20 600/426 |
| 2012/0004518 A1* | 1/2012 | D'Souza | ............... | A61B 5/1135 600/301 |
| 2012/0014501 A1 | 1/2012 | Pelc et al. | | |
| 2012/0155611 A1 | 6/2012 | Ein-Gal | | |
| 2013/0163723 A1* | 6/2013 | Tacke | ............... | A61N 5/1067 378/65 |

OTHER PUBLICATIONS

Han, Inho, Authorized Officer; PCT Search Report and Written Opinion from related PCT/US2013/059154 dated Dec. 18, 2013; 12 pages.

* cited by examiner

*Primary Examiner* — Phillip A Johnston
(74) *Attorney, Agent, or Firm* — Fitch, Even, Tabin & Flannery LLP

(57) ABSTRACT

A radiation device directs a beam of radiation onto a target. The beam can be adjusted using, for example, a control for setting beam shape and a control for setting beam intensity. The target is supported on a surface that can be adjusted using, for example, a control for setting surface position and a control for setting a speed for moving the surface. Controls are selected to adjust the beam and the surface cooperatively in order to compensate for movement of the target.

13 Claims, 5 Drawing Sheets

MULTI-AXIS DYNAMIC TRACKING FOR RADIATION THERAPY

BACKGROUND

The use of radiation therapy for the treatment of cancer is well known. Typically, radiation therapy involves focusing a beam of radiation (e.g., proton, x-ray, or electron radiation) onto a target volume to diagnose an afflicted area or to monitor a tumor or lesion. A beam of high energy proton, x-ray, or electron radiation ("therapeutic radiation") is subsequently directed into the monitored area to treat the area. During treatment, the area continues to be monitored to ensure appropriate positioning of the therapeutic radiation beam.

A radiation therapy device typically includes a surface (e.g., a couch) to support the patient and an overhead radiation source that emits the therapeutic radiation beam. The radiation source directs the beam into the targeted volume (e.g., the tumor being treated) in the patient, who is positioned directly below the radiation source while in a supine position on the couch. The radiation beam may be moved to "paint" the target volume, or the radiation beam may be shaped so that its cross-section approximates the shape of the target volume, so that the beam falls only on the target volume and not on surrounding, healthy tissue. The strength or intensity of the beam is selected depending on the thickness of the target volume and its depth within the patient, as well as other factors.

During treatment, the patient may move. For example, the patient may shift and/or rotate his or her body during treatment, changing both the focal point of the incident radiation beam and the angle of the beam relative to the targeted volume. As a result, the beam may no longer be pointed at just the target volume, and/or the cross-section of the beam at the point where it intersects the target volume may change so that it no longer approximates the shape of the target volume. Consequently, the radiation beam may not cover the entire target volume or might land on tissue outside the target volume.

The target volume itself may move during treatment even if the patient does not. For example, the patient's breathing may cause the target volume to move up and down and hence closer to and then further away from the radiation source. When the target volume is closer to the radiation source, the radiation beam might not cover the entire target volume, and when the target volume is further away from the radiation source, the beam might also land on tissue outside the target volume. Also, the intensity of the beam at the target volume may alternately increase and decrease, and consequently the target volume might not receive a uniform dose of radiation or might not receive the total dose prescribed in the treatment plan.

SUMMARY

Therefore, either the radiation source or the patient (that is, the surface on which the patient is laying) must be moved to compensate for any movement of the target volume. Conventionally, this is accomplished by changing one setting at a time. For example, the shape of the radiation beam might be changed, or the dose rate might be changed.

Embodiments according to the present invention are directed to a multi-axis dynamic tracking system that adapts (adjusts) different controls and their respective settings concurrently and cooperatively to compensate for movements of the target volume. As used herein, an axis may refer to a physical, machine axis (e.g., the position of a leaf or leaves in the multi-leaf collimator used to shape the radiation beam) or a logical axis (e.g., a prescribed part of the treatment plan, such as dose rate). An axis might also be referred to as a modality. In essence, the radiation therapy device and the treatment plan offer numerous degrees of freedom that can be exploited to continuously adapt the radiation treatment delivery to changes in the target and its surroundings. Embodiments according to the present invention advantageously utilize those degrees of freedom concurrently and in combination with one another to compensate for movement of the target volume.

In one embodiment, the beam can be adjusted using, for example, a control for setting beam shape and a control for setting beam intensity. The target is supported on a surface that can be adjusted using, for example, a control for setting surface position and a control for setting a speed for moving the surface. Controls are used concurrently to adjust the beam and the surface cooperatively in order to compensate for movement of the target. Specific examples of how multiple axes can be cooperatively used to dynamically track and treat a target volume are presented in the discussion to follow.

In general, embodiments according to the present invention improve (decrease) response time to target changes, increase tracking accuracy, increase patient comfort, and facilitate quality assurance. These and other objects and advantages of the various embodiments of the invention will be recognized by those of ordinary skill in the art after reading the following detailed description of the embodiments that are illustrated in the various drawing figures.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Figure 1:
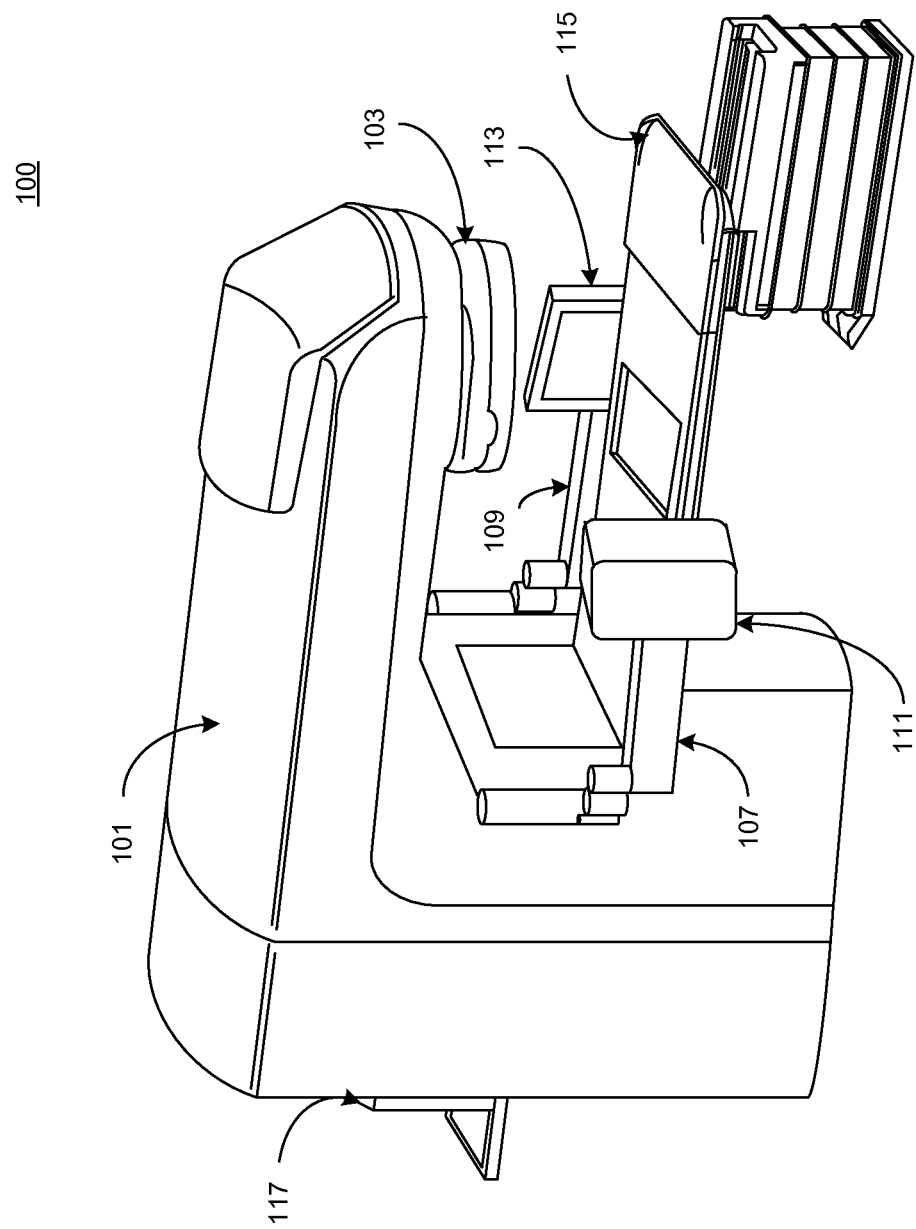
FIG. 1 is an example of a radiotherapy device upon which embodiments according to the present invention can be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

Portions of the detailed description that follows are presented and discussed in terms of a method. Although steps and sequencing thereof are disclosed in a figure herein (e.g., FIG. 6) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

With reference now to FIG. 1, an illustration of an example of a radiation therapy device 100 is depicted, in accordance with one embodiment of the present invention. In one configuration, the radiation therapy device 100 includes a support structure (e.g., a gantry 101), a therapeutic radiation source 103, a number of robotic arms (e.g., robotic arms 107 and 109), a diagnostic radiation source 111, a diagnostic radiation imager 113, and a patient couch 115. In some embodiments, the radiation therapy device 100 may include a control subsystem 117 that includes a communicatively coupled computing device having a processor and a memory.

In one embodiment, the end of the gantry 101, positioned above the patient couch 115, is attached to a therapeutic radiation source 103. The robotic arms 107 and 109 are mounted on the gantry 101. In some embodiments, the robotic arms 107 and 109 may be extendable and retractable. In some embodiments, the robotic arms 107 and 109 are independent from each other and opposable. In one embodiment, a diagnostic radiation source 111 is coupled to the end of a robotic arm (e.g., the robotic arm 107) extending towards patient couch 115. In further embodiments, a diagnostic radiation imager 113 is coupled to the end of an alternate robotic arm (e.g., robotic arm 109), also extending towards patient couch 115. The robotic arms 107 and 109 are capable of maneuvering to allow for positioning of the diagnostic radiation source 111 and the diagnostic radiation imager 113 to any position in space within the travel range of the robotic arm; each of the robotic arms 107 and 109 is capable of pivoting at different pivot points and along a number of independent axes. In still further embodiments, the gantry 101 is also rotatable along one or more axes, allowing for even greater travel ranges for the plurality of robotic arms 107 and 109 and for movement of the therapeutic radiation source 103.

While receiving treatment, a patient is positioned (typically supine) on patient couch 115. A target volume (generally disposed within or about the patient subject) is acquired. According to one embodiment, the target volume is acquired by generating a volumetric image of the area within the patient. A volumetric image of the area is acquired by, for example, generating a three dimensional image using diagnostic radiation source 111 in conjunction with diagnostic radiation imager 113. In one embodiment, diagnostic radiation source 111 may comprise, for example, an x-ray radiation source. The robotic arm 107 attached to diagnostic radiation source 111 can be positioned about the target volume for computer tomography images using a cone x-ray beam to acquire volumetric information. Positioning of the robotic arm 107 may be performed by movement of the robotic arm 107 which may include, but is not limited to, rotating, swiveling, extending and retracting the robotic arm.

In one embodiment, diagnostic radiation source 111 and diagnostic radiation imager 113 may be positioned around a target volume such that the target volume is between the diagnostic radiation source 111 and diagnostic radiation imager 113 while volumetric imaging is being acquired. The radiation (e.g., x-rays) emitted by the diagnostic radiation source 111 travel through the target subject, are received by the diagnostic radiation imager 113 and an image of the target subject is thus generated, in accordance with conventional techniques. The imaging generated from the diagnostic radiation process is subsequently utilized to provide targeting information which can be used to accurately direct the therapeutic radiation from therapeutic radiation source 103 to the target volume from various angles.

In one embodiment, the diagnostic radiation imager 113 can be attached to a second robotic arm 109 opposite from the robotic arm 107 attached to diagnostic radiation source 111. In further embodiments, the robotic arm 109, though still independent of, attached to the diagnostic radiation imager 113 is positioned in concert with the robotic arm 107, such that the diagnostic radiation imager 113 is in constant alignment to diagnostic radiation source 111 and on a side opposite diagnostic radiation source 111 with respect to the target volume.

Once aligned, diagnostic radiation (e.g., an x-ray beam) from the diagnostic radiation source 111 is propagated toward the target volume that is situated on or about the patient couch 115. The diagnostic radiation passes through the target volume and is received by the diagnostic radiation imager 113. The resulting image(s) generated by the diagnostic radiation imager 113 may then be used to reposition the patient using the patient couch 115 to achieve a greater degree of accurate targeting. The therapeutic radiation source 103 subsequently propagates the therapeutic radiation into the target volume within the repositioned patient.

The control subsystem (computing device) 117 may be mounted on the gantry 101, or may be coupled to the radiation therapy device 100, via one or more data transport cables. In further embodiments, control subsystem (computing device) 117 may communicate remotely with the radiation therapy device 100. Once initiated, an imaging acquisition process may position the robotic arms 107 and 109 coupled to the diagnostic radiation source 111 and diagnostic radiation imager 113 to acquire a volumetric image.

As discussed above, a volumetric image may be constructed from images acquired by positioning the diagnostic radiation source 111 and diagnostic radiation imager 113. Once a volumetric image has been constructed for a target volume, the target volume may be repositioned (e.g., by repositioning the patient) to receive therapeutic radiation from the therapeutic radiation source 103 such that the therapeutic radiation may be directed into the target volume with greater precision with respect to the original (or former) position of the target volume (patient). In one embodiment, the therapeutic radiation source 103 can be repositioned relative to the target volume by moving the gantry 101.

Generally speaking, the radiation therapy device 100 utilizes a dynamic tracking system and process to continuously adapt the radiotherapy treatment delivery fraction to changes in the target volume and its surroundings. To do so, the pre-planned positions of the various physical and logical axes provided by the device 100 are adjusted to account for changes that affect the relationship between the therapeutic radiation source 103 and target, such as changes in position, orientation, and shape. An "axis" may refer to any physical machine axis, such as the position of the couch 115, or a logical axis, such as the dose rate delivered to the target. An axis may also be referred to as a modality or degree of freedom and, generally speaking, refers to any of the controls, control settings, or other variables that can be used to manage the treatment of the target volume. Examples include, but are not limited to:

multi-leaf collimator (MLC) leaves and carriages;
gantry and collimator rotation;
couch translational axes (e.g., vertical, longitudinal, and lateral);
couch rotational axes (e.g., rotation, pitch, and roll);
collimation of x-ray sources used for imaging purposes (e.g., kV blades);

dose rate; and
execution speed of treatment.

In general, in one embodiment, the types of axes can be characterized as a first group of controls that control, for example, the shape and intensity of the therapeutic radiation beam, and a second group of controls that control, for example, the position (including orientation) and movement (e.g., speed of movement) of the couch 115 and hence the position and movement of the target. In one embodiment, the types of axes also include a third group of controls that control, for example, the position and movement of the therapeutic radiation source 103 and imager 113, and the shape and intensity of the diagnostic beam.

In embodiments according to the present invention, a multi-axis dynamic tracking system is introduced in order to adapt (adjust) multiple axes at or about the same time (in parallel with one another) during delivery of the treatment fraction to compensate changes in the relative positions (including their relative orientation) of the therapeutic radiation source 103 and the target. If the target moves, for example, then an objective of the multi-axis dynamic tracking system is to adjust the various controls and settings to compensate for that movement, such that the target continues to receive treatment as if it had not moved. The axes may be adjusted independent of each other, although the effect of adjusting one axis may affect the relationship between the target and another axis.

FIGS. 2A, 2B, 3, 4, 5A, and 5B illustrate examples of different axes that, when used concurrently and cooperatively, beneficially compensate for target movement during treatment. First, examples are presented to demonstrate some of the ways that axes can be adjusted to compensate for target movement, and then other examples are presented to demonstrate some of the ways that multiple axes can be adjusted concurrently and cooperatively to better compensate for target movement according to embodiments of the present invention.

Figure 2A:
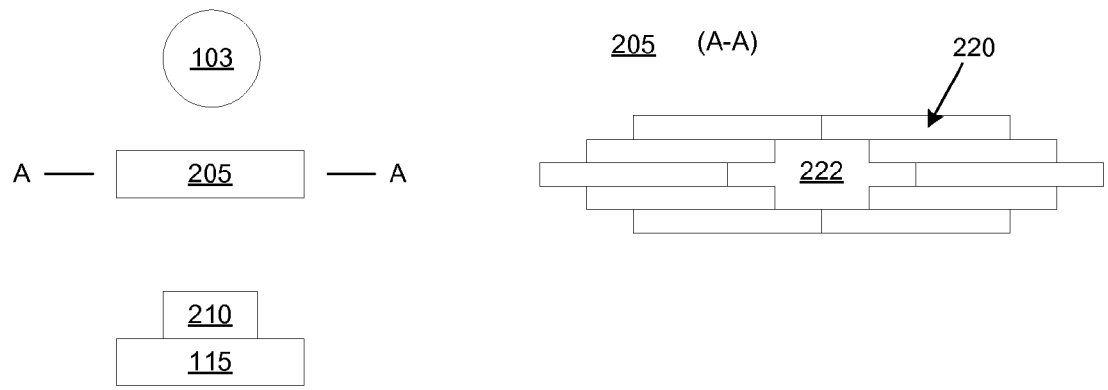
FIGS. 2A, 2B, 3, 4, 5A, and 5B illustrate different axes that can be controlled/adjusted concurrently and cooperatively to compensate for target movement according to embodiments of the present invention.
Figure 2B:
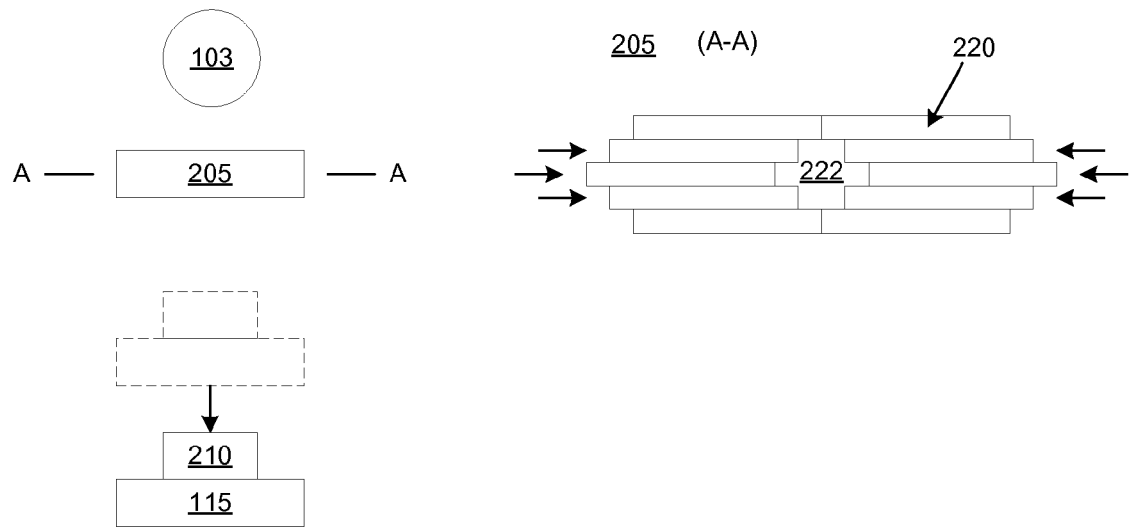

FIGS. 2A and 2B illustrate an example of how beam shape can be controlled to compensate for target movement. More specifically, beam shape can be controlled to compensate for movement of a target toward and away from a radiation source (longitudinal movement and/or vertical movement). For example, the target may move toward the radiation source when the patient inhales, and then move away from the radiation source when the patient exhales (or vice versa).

FIG. 2A illustrates a representation of a target 210 on a couch 115 below a radiation source 103 (e.g., a view from the foot of the couch), and also includes a representation of an MLC 205 situated between the radiation source and the target. To compensate for any up-and-down movement of the target 210, the leaves 220 of the collimator can be moved so that the aperture 222 is wider when the target is closer to the radiation source 103 and narrower when the target is further away, as shown in FIG. 2B. The leaves 220 can be moved at a rate that corresponds to the rate at which the target 210 is moving. At the same time, the dose rate can be increased when the target is closer to the radiation source and decreased when the target is further away, to keep the dose rate to the target volume the same.

Figure 3:
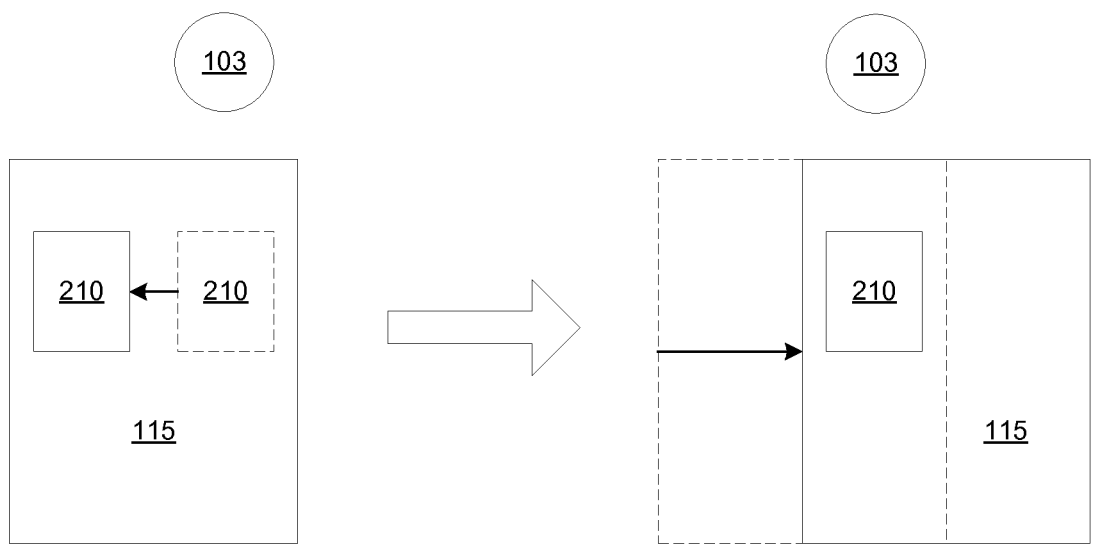

FIG. 3 illustrates an example of how couch position can be controlled to compensate for target movement. FIG. 3 illustrates a representation of a target 210 on a couch 115 (a top-down view). In this example, the target 210 moves in one direction, thus changing its position relative to the radiation source 103. To compensate, the couch 115 (and hence the target 210) can be moved in the opposite direction, so that the position of the target relative to the radiation source 103 is unchanged.

Figure 4:
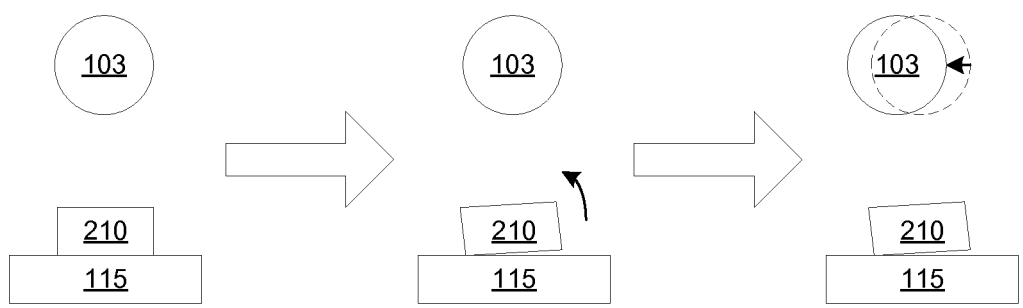

FIG. 4 illustrates an example of how the position of the radiation source can be controlled to compensate for target movement. FIG. 4 illustrates a representation of a target 210 on a couch 115 (e.g., a view from the foot of the couch). In this example, the target 210 moves (rotates) in one direction, thus changing its position relative to the radiation source 103. To compensate, the radiation source 103 can be moved in the same direction, so that the position of the target relative to the radiation source is unchanged.

Figure 5A:
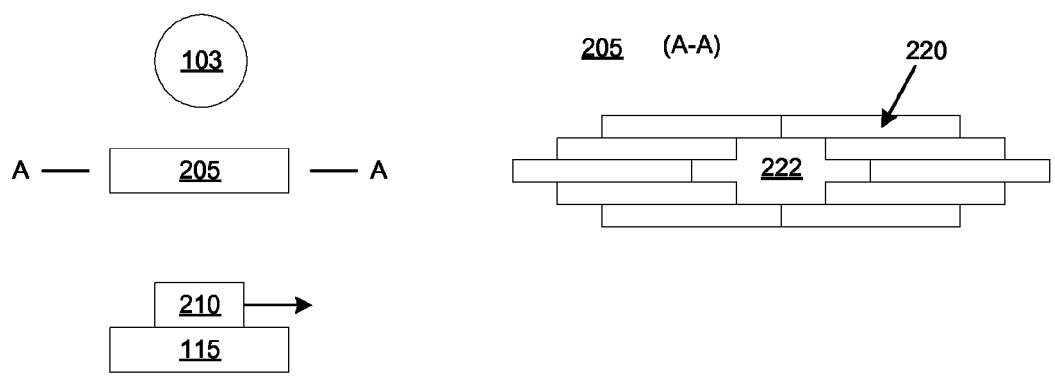
Figure 5B:
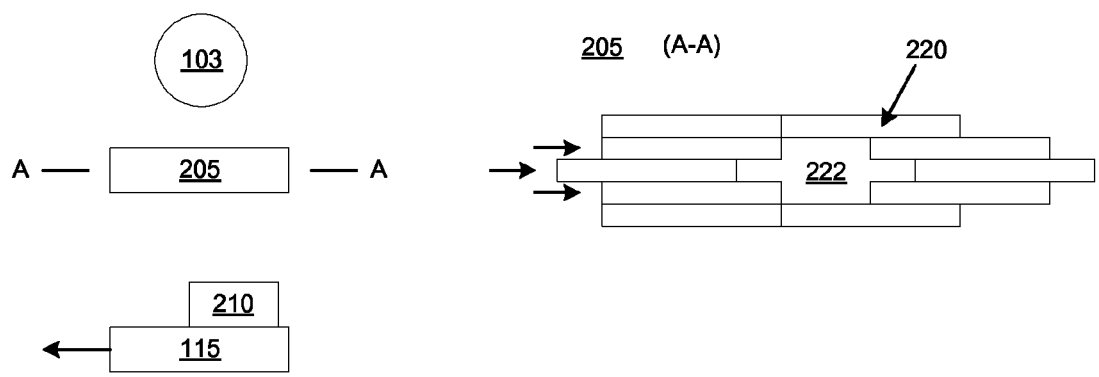

FIGS. 5A and 5B illustrate an example of how the positions of the couch and the MLC leaves can be controlled to compensate for target movement. FIG. 5A illustrates a representation of a target 210 on a couch 115 below a radiation source 103 (e.g., a view from the foot of the couch), and also includes a representation of an MLC 205 situated between the radiation source and the target. In this example, the target 210 moves in one direction, thus changing its position relative to the radiation source 103. To compensate, the leaves 220 of the MLC 205 are moved in the same direction as the target 210 while the couch 115 is moved in the opposite direction, as shown in FIG. 5B. As the target 210 is returned to a position underneath the radiation source 103 due to the movement of the couch 115, the leaves 220 continue to be adjusted, so that when the target returns to a position underneath the radiation source (that is, the relative positions of the radiation source and target are the same as they were before the target moved), the leaves are in the same position that they were in before the target moved.

FIGS. 5A and 5B also demonstrate an example in which the target 210 moves (drifts) in one direction, thus changing its position relative to the radiation source 103. To compensate, the leaves 220 of the MLC 205 are moved in the same direction as the target 210, as shown in FIG. 5B, while the couch 115 initially remains stationary. As the target 210 continues to move, the leaves 220 also continue to move. At some point, the leaves 220 may reach the end of their range of motion (that is, they may reach their extremum—maximum or minimum—setting). To compensate, the couch 115 can be moved in the direction opposite to the direction of movement of the target 210, allowing the leaves to be moved to a position back toward the middle of their range of motion. If the target 210 continues to drift, the leaves 220 can then be adjusted to compensate until they again reach the end of the their range of motion, at which point the couch can again be moved, and so on.

The examples above do not represent all of the possible axes nor all the ways the selected axes might be used. Below, examples of schemes in which axes are cooperatively and concurrently adjusted to improve the treatment of a target by compensating for movement of that target are described. The examples below do not represent all of the possible ways that axes can be combined. Also, although the schemes are described individually, combinations of those schemes can be used. Furthermore, the change in settings that are described in the following examples can be accomplished manually (e.g., in response to direct inputs from an operator), automatically (e.g., according to a preprogrammed treatment plan), or a combination thereof. Moreover, in each of the schemes discussed below, as well as in other schemes according to the present invention, it is not necessary to turn off the radiation beam during tracking (compensation of target movement). In other words, the radiation beam can remain on while axes are adjusted.

In one multi-axis dynamic tracking scheme, the target movement, such as changes in the target volume's position, orientation, or shape (e.g., the cross-section or silhouette presented to the incident radiation beam), is logically separated into different components or modalities, such as velocity or clinical cause. The target's movement is compensated for by concurrently adjusting different axes that are intelligently selected because they match those components. Generally speaking, in this scheme, the movement of the target includes two asynchronous movements (not happening at the same time or speed) and, to compensate for the movement, a first control is selected and adjusted to compensate for the first of the movements, and a second control is selected and adjusted to compensate for the second of the movements.

For example, to track a target that is moving because of respiratory motion, the target motion can be separated into a transient part (e.g., the part due to the respiratory motion) and a baseline part (e.g., changes due to movement of the patient or drifting of the target). To compensate for the transient part, an axis capable of faster motion can be selected and adjusted, while an axis capable of slower motion can be selected to compensate for the baseline part and adjusted. In operation, the controls for the selected axes are adjusted from their current settings to new, different settings. For example, the setting for the MLC control is dynamically changed to compensate for the transient part, while the setting for the couch control is changed to compensate for the baseline part.

In another multi-axis dynamic tracking scheme, the rotational part of the target's motion is compensated for with a rotational axis, and the translational part of the target's motion is compensated for with a translational axis. As the first axis is adjusted, the second axis is also adjusted to account for not only the target's motion but also the effect (if any) of the adjustment of the first axis. In general, in this scheme, a first control is selected and adjusted to compensate for movement around a rotational axis, and a second control is selected and adjusted to compensate for movement along a translational axis.

Another multi-axis dynamic tracking scheme combines multiple axes that, together, allow compensation for target motion to be achieved more quickly than could be achieved using one of the axes by itself. For example, couch motion and MLC leaf motion (aperture adaptation) can be combined, or MLC leaf and carriage motion can be combined, to compensate for target motion faster than could be achieved using any one of the selected axes. In general, in this scheme, a first control and a second control are selected and adjusted, where controls are selected such that they synergistically compensate for the movement.

Similarly, if the position of the target volume drifts in one direction over time, then the leaves 220 can be adjusted to match that drift until the leaves reach the end of their range of motion, at which time the couch 115 can be adjusted while the leaves are moved back to a point toward the middle of their range of motion.

Yet another multi-axis dynamic tracking scheme compensates for target motion by recognizing that different axes have different time-related behavior. For instance, the couch 115 may move slower than the leaves 220 of the MLC 205. The MLC 205 may thus provide the best way to compensate for target movement in the shorter term; however, for various reasons, the couch 115 may provide the best mechanism for compensating target movement in the longer term (e.g., the range of motion may be greater for the couch than for the MLC, so moving the couch may provide more flexibility for any further movement of the target volume). In this scheme, first the couch 115 is moved to attempt to compensate for target movement. The residual target motion that the slower couch 115 cannot follow is compensated for using the faster leaves 220. As the couch 115 continues to move to a final position, the leaves 220 also continue to be adjusted to account for the couch's movement.

Thus, the scheme just described adapts multiple axes transiently, in particular axes that behave differently. In general, in such a scheme, a first control and a second control are selected and adjusted, where the first control reaches a first target setting before a second control reaches a second target setting; the first control is subsequently held at the first target setting until the second control reaches the second target setting; and then the first control is adjusted to a different setting that complements the second target setting in terms of compensating for target movement.

In another scheme, multi-axis dynamic tracking is used to improve the accuracy of the compensation. For example, the MLC 205 can be used to accurately track target movement, but its accuracy is limited by the width of the individual leaves 220. In other words, a leaf can be moved to change the width of the aperture to compensate for target movement, but the change in width will be a discrete amount corresponding to the width of the leaf that is moved. In this situation, accuracy can be improved by combining movement of the leaves 220 with adaptation of another axis capable of more discrete movement (e.g., the couch 115). That is, a leaf of the MLC 205 can be moved to change the aperture to compensate for target movement to the tolerance provided by that axis, and the couch 115 can also be moved a relatively small distance to improve accuracy to something less than the tolerance that can be achieved by the MLC alone. In general, in this scheme, a first control is selected and adjusted to an extremum setting (e.g., its minimum tolerance, or perhaps its maximum range of motion as in the previous example) and a second control is selected and adjusted until the movement of the target is compensated.

The multi-axis dynamic tracking scheme or schemes to be used to compensate target movement can be intelligently selected depending on a number of considerations including, for example, patient comfort, the objective of the treatment plan, and the characteristics of the axes themselves. For example, rapid movement of the couch 115 may be uncomfortable for the patient, and so the couch is instead moved slowly. Thus, the couch can be selected to compensate smaller target movements, but larger movements are compensated using one of the other axes that can be moved rapidly without affecting the comfort of the patient. Thus, in one embodiment, the various axes can be ranked based on their capabilities (e.g., the speed at which they can respond to target movement, their degree of precision, etc.) as a function of the type of movement (e.g., toward or away from the incident radiation beam versus movement orthogonal to the beam). In one such embodiment, the ranking of each axis can also be weighted by its affect on patient comfort. Based on the type of target movement, the ranking can be used to select the most appropriate axis to be adjusted; the amount of compensation that can be achieved with that axis can be predicted or measured; another axis can then be selected based on the ranking; the amount of compensation that can be achieved considering both axes can be determined; and so on, until compensation for target movement is accomplished.

Figure 6:
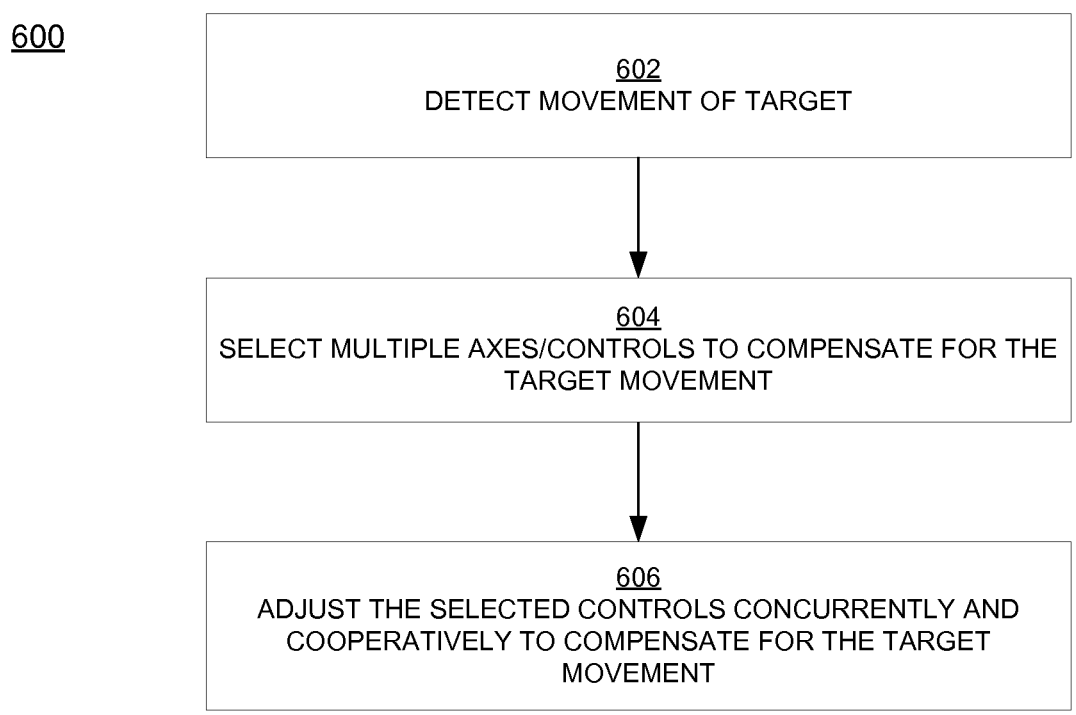
FIG. 6 is a flowchart of an example of a method for operating a radiation therapy device in accordance with embodiments of the present invention.

FIG. 6 is a flowchart 600 of an example of a method for operating a radiation device (e.g., device 100 of FIG. 1) in accordance with one embodiment of the present invention. Although specific steps are disclosed in the flowchart 600, such steps are exemplary. That is, the present invention is well suited to performing various other steps or variations of the steps recited in the flowchart 600. In one embodiment, the flowchart 600 is implemented as program instructions stored in a computer-readable memory unit of a control subsystem (e.g., control subsystem 117 of FIG. 1).

In block 602, movement of a target relative to an incident beam of radiation is detected. In one embodiment, the beam is projected from a moveable radiation source and is adjustable using variable beam controls that include, for example, a variable control for setting beam shape and a variable control for setting beam intensity, and the target is supported by a moveable surface that is adjustable using variable surface controls that include, for example, a variable control for setting surface position and a variable control for setting a speed for moving the surface.

In block 604, controls are selected from the aforementioned variable controls. For example, the selected controls may include one or more of the surface controls and one or more of the beam controls. In block 606, the selected controls are adjusted concurrently and cooperatively to compensate for the movement of the target.

In summary, embodiments according to the present invention provide dynamic target tracking using multiple axis of a radiation therapy device at the same time during the course of treatment. Axes can be intelligently selected depending on their characteristics considering the type of target movement and the objective(s) of the treatment plan, and also considering patient comfort. Because axes can be combined, a treatment plan can be implemented with more flexibility. The response time to compensate target movement, the accuracy of the compensation, and patient comfort are thus improved. Because the radiation beam can remain on while axes are adjusted, treatment of the target volume is continuous even while target movement is compensated; thus, a radiotherapy session can be completed more quickly, further enhancing patient comfort. Quality assurance is facilitated by clear arbitration between the different axes.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for configuring a radiation device, said system comprising:
   variable beam controls operable for configuring a radiation beam, said variable beam controls comprising a variable control for setting beam shape and a variable control for setting beam intensity;
   variable surface controls operable for configuring a surface that supports a target of said radiation beam, said variable surface controls comprising a variable control for setting surface position and a variable control for setting a speed for moving the surface; and
   a control subsystem coupled to said variable beam controls and said variable surface controls, said control subsystem operable for detecting movement of said target relative to said radiation beam and also operable for selecting controls from said variable beam controls and from said variable surface controls including specifically the variable control for setting the speed for moving the surface by, at least in part, use of a multi-axis dynamic tracking scheme that includes selecting a most appropriate axis to be adjusted as a function of a type of target movement, wherein the selected controls are used cooperatively to compensate for said movement while the radiation beam is on.

2. The system of claim 1 wherein said movement of said target comprises two asynchronous movements, wherein said selected controls comprise a first control that is adjusted to compensate for the first of said movements and a second control that is adjusted to compensate for the second of said movements.

3. The system of claim 1 wherein said movement comprises a first movement around a rotational axis and a second movement along a translational axis, wherein said selected controls comprise a first control that is adjusted to compensate for said first movement and a second control that is adjusted to compensate for said second movement.

4. The system of claim 1 wherein said selected controls comprise a first control and a second control that are adjusted to synergistically compensate for said movement.

5. The system of claim 1 wherein said selected controls comprise a first control that reaches a first target setting before a second control reaches a second target setting, wherein said first control is subsequently held at said first target setting until said second control reaches said second target setting and then adjusted to a different setting that complements said second target setting.

6. The system of claim 1 wherein said selected controls comprise a first control and a second control, wherein said first control is adjusted to an extremum setting and said second control is adjusted until said movement of said target is compensated.

7. The system of claim 1 further comprising variable source controls comprising a variable control for setting a position of said radiation source and a variable control for setting a speed for moving said radiation source, wherein controls selected from at least two of said variable beam controls, said variable surface controls, and said variable source controls are used cooperatively to compensate for said movement of said target.

8. A method of operating a radiation device, said method comprising:
  detecting movement of a target relative to an incident beam of radiation, said beam projected from a moveable radiation source and adjustable using variable beam controls comprising a variable control for setting beam shape and a variable control for setting beam intensity, said target supported by a moveable surface that is adjustable using variable surface controls comprising a variable control for setting surface position and a variable control for setting a speed for moving the surface;
  selecting controls from said variable beam controls and from said variable surface controls including selecting the variable control for setting the speed for moving the surface by, at least in part, use of a multi-axis dynamic tracking scheme that includes selecting a most appropriate axis to be adjusted as a function of a type of target movement; and
  adjusting the selected controls concurrently and cooperatively while the beam of radiation is on to compensate for said movement of said target.

9. The method of claim 8 wherein said movement of said target comprises two asynchronous movements, wherein said method comprises:
  adjusting a first control to compensate for the first of said movements; and
  adjusting a second control to compensate for the second of said movements.

10. The method of claim 8 wherein said movement comprises a first movement around a rotational axis and a second movement along a translational axis, wherein said method comprises:
  adjusting a first control to compensate for said first movement; and
  adjusting a second control to compensate for said second movement.

11. The method of claim 8 wherein said method comprises adjusting a first control and a second control that synergistically compensate for said movement.

12. The method of claim 8 wherein the selected controls comprise a first control that reaches a first target setting before a second control reaches a second target setting, wherein said method further comprises keeping said first control at said first target setting until said second control reaches said second target setting, and then adjusted said first control to a different setting that complements said second target setting.

13. The method of claim 8 wherein said method comprises adjusting said first control to an extremum setting and adjusting said second control until said movement of said target is compensated.

* * * * *